(12) United States Patent
Hongou (10) Patent No.: US 7,843,764 B2
(45) Date of Patent: Nov. 30, 2010

(54) ULTRASONIC IMAGING APPARATUS

(75) Inventor: Hironobu Hongou, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 358 days.

(21) Appl. No.: 12/047,565

(22) Filed: Mar. 13, 2008

(65) Prior Publication Data

US 2008/0225639 A1  Sep. 18, 2008

(30) Foreign Application Priority Data

Mar. 14, 2007  (JP) .............................. 2007-065147

(51) Int. Cl.
*H04B 17/00* (2006.01)
(52) U.S. Cl. ........................................................ 367/13
(58) Field of Classification Search .................. 367/13; 73/1.82
See application file for complete search history.

(56) References Cited

U.S. PATENT DOCUMENTS

2005/0210955 A1\* 9/2005 McCartan et al. ............ 73/1.82
2006/0191315 A1\* 8/2006 McCartan et al. ............ 73/1.82
2008/0225639 A1\* 9/2008 Hongou ....................... 367/13

FOREIGN PATENT DOCUMENTS

| JP | 64-56038 | 3/1989 |
|---|---|---|
| JP | 2000-139905 | 5/2000 |
| JP | 2005-319199 | 11/2005 |

\* cited by examiner

*Primary Examiner*—Dan Pihulic
(74) *Attorney, Agent, or Firm*—Oblon, Spivak, McClelland, Maier & Neustadt, L.L.P.

(57) ABSTRACT

A plurality of signal transmitters are respectively configured to produce a pulse current by repeatedly switching the connection state of a switching element. A plurality of ultrasonic transducers are respectively configured to transmit an ultrasonic pulse to a subject to be examined upon receiving said pulse current, and to produce a receiving current upon receiving the reflected wave. A signal receiver is configured to receive said receiving current. A test signal generator is configured to produce a test signal and to output said test signal to a connection point of said signal transmitter, said ultrasonic transducer, and said signal receiver by switching said connection state of said switching element to a state through which said test signal is conducted.

11 Claims, 7 Drawing Sheets

ULTRASONIC IMAGING APPARATUS

BACKGROUND OF THE INVENTION

1. Field of the Invention

The present invention relates to an ultrasonic imaging apparatus comprising a transmitting circuit and a receiving circuit of ultrasonic signals in an ultrasound probe. More specifically, the present invention relates to an ultrasonic imaging apparatus comprising test circuits of the transmitting circuit and the receiving circuit of ultrasonic signals.

2. Description of the Related Art

Conventionally, for an ultrasonic imaging apparatus that generates an ultrasonic tomographic image by sending out an ultrasound beam to a subject to be examined and receiving the reflected ultrasonic echo, a 1-dimension array probe on which reed-shaped piezoelectric elements are arranged in an array form is used.

Electronic scanning using a 1-dimension array probe allows electronic focusing and scanning of ultrasound beams within a surface in the direction of the arrangement of the piezoelectric elements. However, in the direction perpendicular to the direction of arrangement (i.e., the normal line direction of the ultrasonic scanning surface described above), it allows only focusing by using only an acoustic lens, so changes of the focal point are limited to within a narrow range. Therefore, it is difficult to focus various points on a two-dimensional plane. In addition, it is possible only to two-dimensionally scan an ultrasound beam because the arrangement of array elements is a one-dimensional arrangement.

Therefore, in order to realize omni-directional focusing and high-speed three-dimensional scanning, and to facilitate understanding of the structures within living bodies, a 2-dimension array probe in which ultrasonic transducers are arranged two-dimensionally and that allows delay-controlling in each of the two directions in which ultrasonic transducers are arranged has been proposed in recent years. (For example, see Japanese Unexamined Patent Application Publication 2005-319199.)

Subsequently, three-dimensional scanning has been conducted and stereoscopic images have been displayed by employing the 2-dimension array probe as described.

In addition, for 2-dimension array probes such as those with a 32×32 configuration, the number of transducers required is 1,024. In the 2-dimension array probe having the number of transducers as described, it is necessary to transmit/receive ultrasonic waves by using all transducers. In this case, 1,024 transducers are housed in a probe head to be placed in contact with a subject to be examined, so if they are connected to an ultrasonic imaging apparatus without change, 1,000 or more cables will be needed. The structure of such an ultrasound probe is impractical.

Furthermore, for the 2-dimension array probe, transducer impedance will increase because the shape of transducers is smaller than that of a conventional 1-dimension array probe. As a result, degradation of received echo becomes greater for the 2-dimension array probe. This lowers the amount of information used for forming images and makes proper diagnosis difficult.

Figure 1:
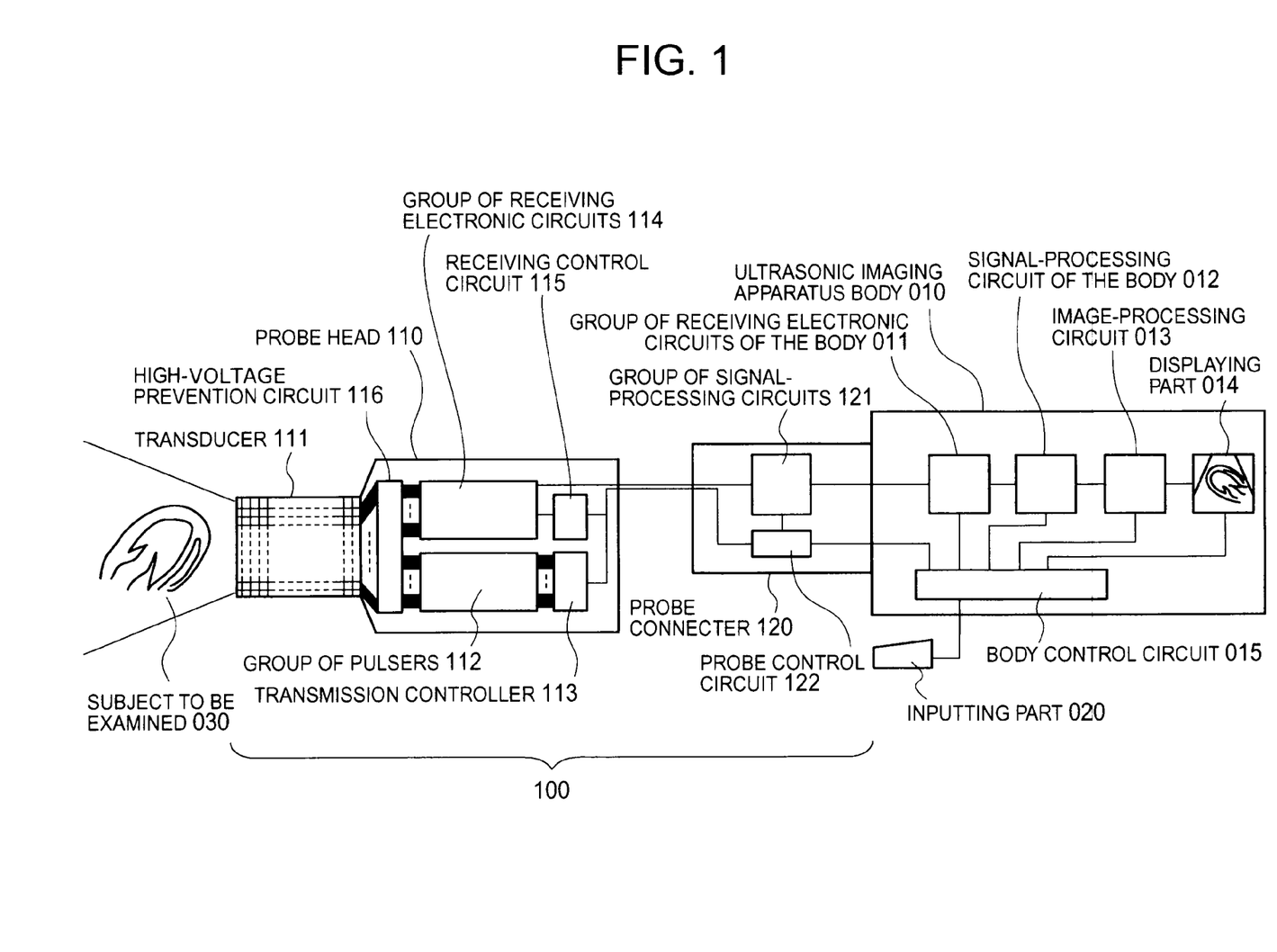
FIG. 1 is a configuration diagram that represents a conventional ultrasonic imaging apparatus.

Therefore, in order to efficiently supply a pulse for transmission and to minimize the degradation of received echoes, an ultrasonic imaging apparatus including a probe head with a configuration as shown in FIG. 1 has conventionally been proposed for the 2-dimension array probe. FIG. 1 is a diagram of a configuration of an ultrasonic imaging apparatus including a conventional 2-dimension array probe. This ultrasonic imaging apparatus, as shown in FIG. 1, incorporates in the probe head 110, a group of pulsers 112 for supplying a transmitted pulse to the proximity of a transducer 111 in a probe head 110, a transmission controller 113 for controlling the group of pulsers 112, a group of receiving electronic circuits 114 for amplifying the received echo, a receiving control circuit 115 for controlling the group of receiving electronic circuits 114, and a high-pressure prevention circuit 116 for protecting the group of receiving electronic circuits 114 from a high-voltage pulse outputted from the group of pulsers 112. Herein, the group of pulsers 112 is an aggregation of a plurality of pulsers, and hereinafter, when explaining one pulser, it is simply referred to as a pulser 112. In addition, hereinafter, an aggregation of a plurality of transducers 111 is referred to as a group of transducers 111.

Upon receiving a control signal such as a pulse production command from a body control circuit 015 that is housed in an ultrasonic imaging apparatus body 010, a probe control circuit 122 conducts a relocation of the data necessary to transmit a control signal or the like. Then, the probe control circuit 122 transmits the control signal to the transmission controller 113. Upon receiving the control signal, the transmission controller 113 transmits a timing signal for a pulse signal to the group of pulsers 112. Upon receiving the timing signal from the transmission controller 113, the group of pulsers 112 generates a pulse signal. The produced pulse signal causes the group of transducers 111 to oscillate and to send out an ultrasound beam to a subject to be examined 030, and then is received as the received echo that is a reflected wave through the group of transducers 111. A received echo signal that is based on the received echo received through the group of transducers 111 is sent to the group of receiving electronic circuits 114. The group of receiving electronic circuits 114 groups a plurality of channels as channels corresponding to the group of transducers 111 and performs local beamforming. This makes it possible to reduce the number of cables for the probe. For example, in the case of the 2-dimension array probe with the 32×32 configuration, assuming that there are 8 channels per group, the group of receiving electronic circuits 114 has 1,024 channels that correspond to the group of pulsers 112, which are reduced to 1,024/8 groups.

The received echo signal to which the local beamforming has been performed, is processed such as buffering in the group of signal-processing circuits 121 housed in a probe connecter 120, and then is entered into the ultrasonic imaging apparatus body 010. Herein, the probe control circuit 122 conducts setting of the group of signal-processing circuits 121 upon receiving a signal from the body control circuit 015. A beamforming is performed for the entire received echo signal in a group of receiving electronic circuits of the body 011. From the received echoes, all of which the received beamforming has been performed upon in the group of receiving electronic circuits of the body 011, an envelope signal corresponding to information in a living body or the like is extracted by a signal-processing circuit of the body 012. Furthermore, the received echo is converted to a desired display coordinate in an image-processing circuit 013 and is displayed on the displaying part 014.

In addition, the body control circuit 015 that is installed in the ultrasonic imaging apparatus body 010 controls each part of the ultrasonic imaging apparatus body 010 in accordance with parameter information entered from an inputting part 020, such as operation mode, scan mode, or display mode.

Figure 2:
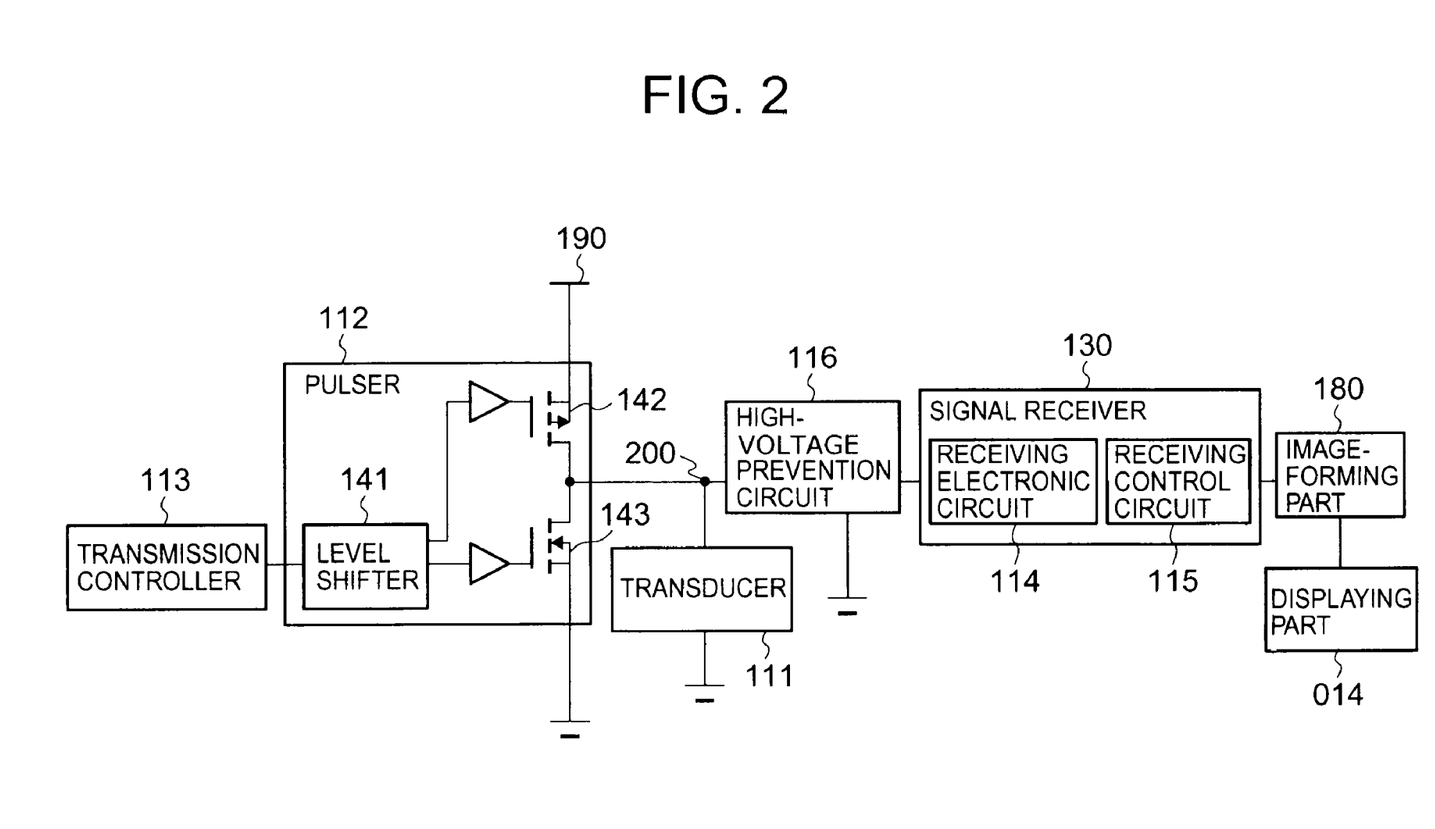
FIG. 2 is the block diagram of a transmitting/receiving circuit when using a conventional unipolar pulser.
Figure 3:
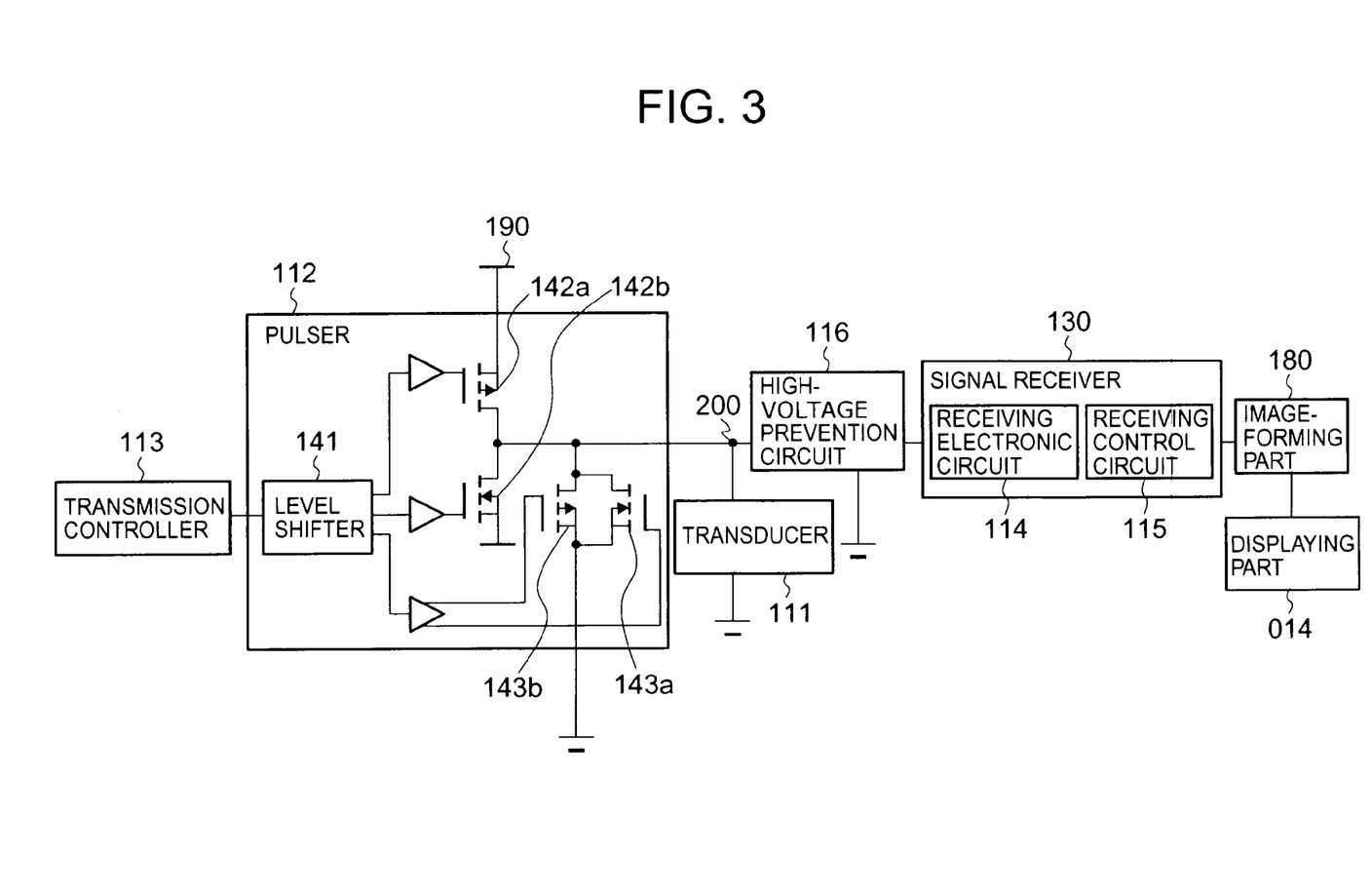
FIG. 3 is the block diagram of a transmitting/receiving circuit when using a conventional bipolar pulser.

FIG. 2 is a diagram that represents the skeletal framework of a transmitting/receiving circuit with one channel when employing a pulser that transmits a unipolar pulse. FIG. 3 is a diagram that represents the skeletal framework of a transmitting/receiving circuit with one channel when employing a pulser that transmits a bipolar pulse.

Next, operations in the case of the unipolar pulser will be explained. As shown in FIG. 2, the pulser 112 has a level shifter 141, a pulse production FET 142, and a shunt field-effect transistor (FET) 143.

The transmission controller 113 transmits a timing signal to the pulser 112. The transmission controller 113 has a circuit that produces a timing signal for instructing the transducer 111 to generate an ultrasonic pulse and a timing signal for receiving a signal based on the ultrasonic echo from the transducer 111. Then, to instruct the transducer 111 to generate an ultrasonic pulse, the transmission controller 113 repeatedly switches the pulse production FET 142 on and off at a constant timing by means of a timing pulse signal, and turns on the shunt FET 143 when the pulse production FET 142 is off. In addition, when receiving from the transducer 111 a received echo signal that is based on the ultrasonic echo, the transmission controller 113 sends a signal for turning off both the pulse production FET 142 and the shunt FET 143.

The level shifter 141 converts the timing pulse entered from the transmission controller 113 into a voltage of several tens of volts and sends a pulse corresponding to the pulse production FET 142 and the shunt FET 143.

The pulse production FET 142 is a switching element for producing a pulse and the shunt FET 143 is a switching element for returning the voltage that has risen to ground the pulse.

When instructing the transducer 111 to generate an ultrasonic pulse (i.e., when sending out an ultrasound beam to the subject to be examined 030), the pulse production FET 142 and the shunt FET 143 output a pulse signal by repeating on/off operations at a constant timing upon receiving a command from the transmission controller 113. At this time, the shunt FET 143 is off when the pulse production FET 142 is on, and the shunt FET 143 becomes on when the pulse production FET 142 turns off. As a result of this, voltage that is increased once by the pulse production FET 142 is grounded instantly. The transducer 111 receives the pulse produced here, and then an ultrasound beam is sent to the subject to be examined 030. Herein, the high-pressure prevention circuit 116 is a diode; a high-voltage pulse sent from the pulser 112 is blocked and not sent to the receiving electronic circuit 114.

When receiving a received echo from the subject to be examined 030, the ultrasound beam is reflected from the subject to be examined 030 and received in the transducer 111 as a received echo. The transducer 111 converts the received echo into a signal and sends the same to the receiving electronic circuit 114. This signal passes through the high-pressure prevention circuit 116 because the voltage thereof is weak. At this time, a transmission/reception controller 113 turns off both the pulse production FET 142 and the shunt FET 143 so that the received echo signal will not flow to the group of pulsers 112. Herein, 'turning off' refers to generating a state of high impedance.

Next, operations of the bipolar pulser 112 will be explained. As shown in FIG. 3, the pulser 112 comprises a level shifter 141, a positive pole pulse production FET 142a, a negative pole pulse production FET 142b, a shunt FET 143a for grounding the voltage of the positive pole pulse production FET 142a, and a shunt FET 143b for grounding the voltage of the negative pole pulse production FET 142b.

Also, in the case of the bipolar pulser 112, as is the case with the unipolar pulser 112, a timing signal for transmission is received from the transmission controller 113, and the level shifter 141 turns the positive pole pulse production FET 142a, the negative pole pulse production FET 142b, the shunt FET 143a, and the shunt FET 143b on and off to produce a bipolar pulse. The transducer 111 receives this pulse and sends out an ultrasound beam to the subject to be examined 030.

Conventionally, for an ultrasonic imaging apparatus having a 1-dimension array probe, an electronic circuit for transmitting/receiving ultrasonic waves (transmitting/receiving circuit) is housed in the ultrasonic imaging apparatus body. This made it possible to conduct an operation test of the transmitting/receiving circuit independently from the ultrasound probe by running a test program in the ultrasonic imaging apparatus body when using the ultrasonic imaging apparatus having a 1-dimension array probe. However, for the ultrasonic imaging apparatus having a 2-dimension array probe as described above, a transmitting/receiving circuit is housed in a probe head. As a result, it became difficult to conduct the operation test of the transmitting/receiving circuit independently from the ultrasound probe by means of the ultrasonic imaging apparatus having a 2-dimension array probe as described above.

In addition, for the abovementioned ultrasonic imaging apparatus, 1,000 or more sets of electronic circuits for performing transmission/reception are housed in the probe head. In other words, the apparatus has 1,000 or more sets of structures in which transducers for actually transmitting/receiving ultrasonic waves, a transmitting circuit for applying a high-pressure pulse to each transducer, and a receiving circuit for amplifying a weak ultrasonic echo received by those transducers are directly connected. Therefore, when there is a local abnormality in those electronic circuits for performing transmissions/receptions, the signal goes missing, likely resulting in an artifact or causing unusual heat generation. However, it is difficult to electrically check whether an enormous electronic circuit is operating properly. Thus, an operation check, for example of an ultrasonic imaging apparatus as described, has been acoustically conducted by transmitting a pulse and receiving an echo for channels of all transducers by means of an external target in which a reflecting plate is placed in a water tank. However, the conventional test method always requires a water tank, and a large amount of labor is necessary to conduct the test. Furthermore, in the conventional test method, the angle setting of the 2-dimension array probe against the external target involves errors for each test, and thus the amplitude of the received echo becomes misaligned for each channel. Therefore, it was difficult to achieve high-integrity test results using the conventional test method.

SUMMARY OF THE INVENTION

As described above, the present invention is intended to provide an ultrasonic imaging apparatus that is capable of conducting a test of an electronic circuit that transmits/receives to each corresponding channel by means of a signal to be tested that has been produced in a probe.

A first aspect of this invention is an ultrasound probe, comprising: a plurality of signal transmitters respectively configured to produce a pulse current by repeatedly switching the connection state of a switching element; a plurality of ultrasonic transducers respectively configured to transmit an ultrasonic pulse to a subject to be examined upon receiving said pulse current, and to produce a receiving current upon receiving the reflected wave; a signal receiver configured to receive said receiving current; and a test signal generator configured to produce a test signal and to output said test signal to a connection point of said signal transmitter, said ultrasonic transducer, and said signal receiver by switching said connection state of said switching element to a state through which said test signal is conducted.

According to this first aspect, when the switching element is fixed to the ground side, a test signal will be sent from the test signal generator that is located in the ultrasound probe. Thus, it is possible to transmit a test signal only when conducting a test and to conduct a test of the ultrasound probe using the test signal generator that is disposed in the ultrasound probe.

A second aspect of this invention is an ultrasound probe, comprising: a transducer, disposed at a predetermined connection point, configured to receive a pulse signal and to send out an ultrasound beam to a subject to be examined; a signal transmitter configured to produce an ultrasonic pulse from said connection point; and a signal receiver configured to receive a signal that is based on an ultrasonic echo from said connection point, wherein the ultrasound probe comprises: a switching part configured to switch two operation modes consisting of an image-forming mode and a test mode; a transmission controller configured to supply said pulse signal from said signal transmitter to said connection point when instructing said transducer to produce said ultrasonic pulse in said image-forming mode, wherein the transmission controller is configured to turn off said signal transmitter in a high output impedance state when instructing said transducer to receive the ultrasonic echo reflected by the subject to be examined in said image-forming mode, and is configured to turn off said signal transmitter in a high output impedance state in said test mode; a test signal outputting part configured to output a test signal to said connection point; and a test controller configured to turn off the output of said test signal from said test signal outputting part in said image mode, wherein the test controller is configured to instruct said test signal outputting part to output said test signal in said test mode.

A third aspect of this invention is an ultrasound probe, comprising: a transducer, disposed at a predetermined connection point, configured to receive a pulse signal and to send out an ultrasound beam to a subject to be examined; a signal transmitter having a first switching element and a second switching element that are connected to said connection point in parallel, the signal transmitter being configured to pulse-drive both said first switching element and said second switching element when instructing said transducer to produce an ultrasonic pulse and configured to turn off said first switching element and said second switching element when instructing said transducer to receive the ultrasonic echo reflected by the subject to be examined; and a signal receiver configured to receive a signal that is based on said ultrasonic echo from said connection point, wherein the ultrasound probe further comprises: a switching part configured to switch between two operation modes consisting of an image-forming mode and a test mode; a test signal outputting part that is connected between said second switching element and said ground in series, wherein the test signal outputting part is configured to output a test signal; a limiter that is connected to said test signal outputting part in parallel, configured to pass a signal outputted from said test signal outputting part through said second switching element; a transmission controller configured to turn off said first switching element and to turn on said second switching element in said test mode; and a test controller configured to operate said test signal outputting part to send out said test signal to said signal receiver in said test mode.

With the ultrasound probe in the first, second, or third aspect, it is possible to transmit a test signal by cutting off the pulser in the test and by connecting the test signal generator that is located in the ultrasound probe. This makes it possible to transmit a test signal to a test apparatus of the ultrasound probe by using a test signal generator that is located in the ultrasound probe only when conducting a test. In addition, a limiter is provided in the third aspect, so it is possible to avoid entering signals other than the test signal into the signal receiver.

A fourth aspect of this invention is an ultrasonic imaging apparatus, comprising an ultrasound probe comprising: a transducer, disposed at a predetermined connection point, configured to receive a pulse signal and to send out an ultrasound beam to a subject to be examined; a signal transmitter having a first switching element and a second switching element that are connected to said connection point in parallel, the second switching element being configured to pulse-drive both said first switching element and said second switching element when instructing said transducer to produce an ultrasonic pulse and configured to turn off said first switching element and said second switching element when instructing said transducer to receive the ultrasonic echo reflected by said subject to be examined; and a signal receiver configured to receive a signal that is based on said ultrasonic echo from said connection point, and an image-generating part configured to generate an ultrasonic image based on the signal received from said ultrasound probe and to display the same on a displaying part, wherein said ultrasound probe further comprises: a switching part configured to switch between two operation modes consisting of an image-forming mode and a test mode; a test signal outputting part, connected between said second switching element and said ground in series, configured to output a test signal, a limiter, connected to said test signal outputting part in parallel, configured to obtain a signal outputted from said test signal generator through said second switching element; a transmission controller configured to turn off said first switching element and to turn on said second switching element in said test mode; and a test controller configured to operate said test signal outputting part to send out said test signal to said signal receiver in said test mode, and wherein said image-forming part is configured to compare said test signal received from said signal receiver with a threshold stored in advance and to instruct said displaying part to display a warning in test mode when exceeding said threshold.

With the ultrasonic imaging apparatus of this fourth aspect, it is possible to determine in the image-forming part, by using the test signal entered from the test signal generator that is located in the ultrasound probe in the test mode, whether there are any abnormalities in the ultrasound probe. This makes it possible to conduct a test of the ultrasound probe by using the test signal outputted from the test signal generator that is located in the ultrasound probe.

A fifth aspect of this invention is an ultrasound probe, comprising: a transducer, disposed at a predetermined connection point, configured to receive a pulse signal having a polarity of positive and negative and to send out an ultrasound beam to a subject to be examined; a signal transmitter having two first switching elements and two second switching elements, the two first switching elements being connected to said connection point in parallel and respectively having polarity of positive and negative, two second switching elements pairing with said first switching elements, wherein the signal transmitter is configured to pulse-drive both said two first switching elements and said two second switching elements when instructing said transducer to produce an ultrasonic pulse, wherein the signal transmitter is configured to turn off said two first switching elements and said two second switching elements when instructing said transducer to receive the ultrasonic echo reflected by the subject to be examined; and a signal receiver configured to receive a signal that is based on said ultrasonic echo from said connection point, wherein said ultrasound probe further comprises: a switching part configured to switch between two operation modes consisting of an image-forming mode and a test mode; a test signal outputting part that is connected between said second switching element and said ground in series, configured to output a test signal; a limiter that is connected to said test signal outputting part in parallel, configured to obtain a signal sent from said test signal generator through said second switching element; a transmission controller configured to turn off both said two first switching elements and to turn on any one or both of said two second switching elements in said test mode; and a test controller configured to operate said test signal outputting part to send out said test signal to said signal receiver in said test mode.

With the ultrasonic imaging apparatus of this fifth aspect, it is possible to transmit a test signal to a test apparatus of the ultrasound probe using the test signal generator that is located in the ultrasound probe only when conducting a test for the ultrasound probe that uses a bipolar pulser.

DETAILED DESCRIPTION OF THE EMBODIMENTS

First Embodiment

Figure 4:
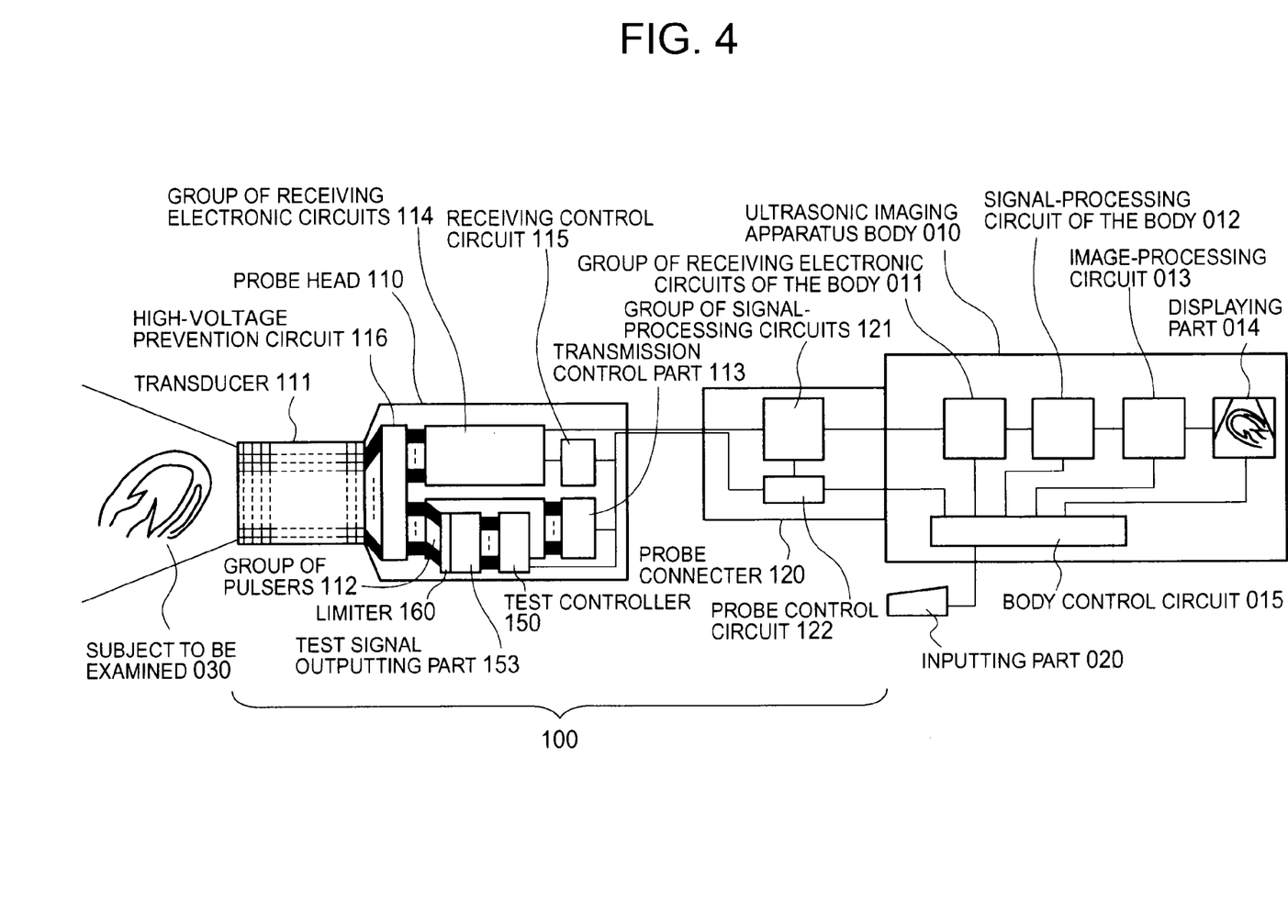
FIG. 4 is a configuration diagram that represents an example of the ultrasonic imaging apparatus according to the present invention.
Figure 5:
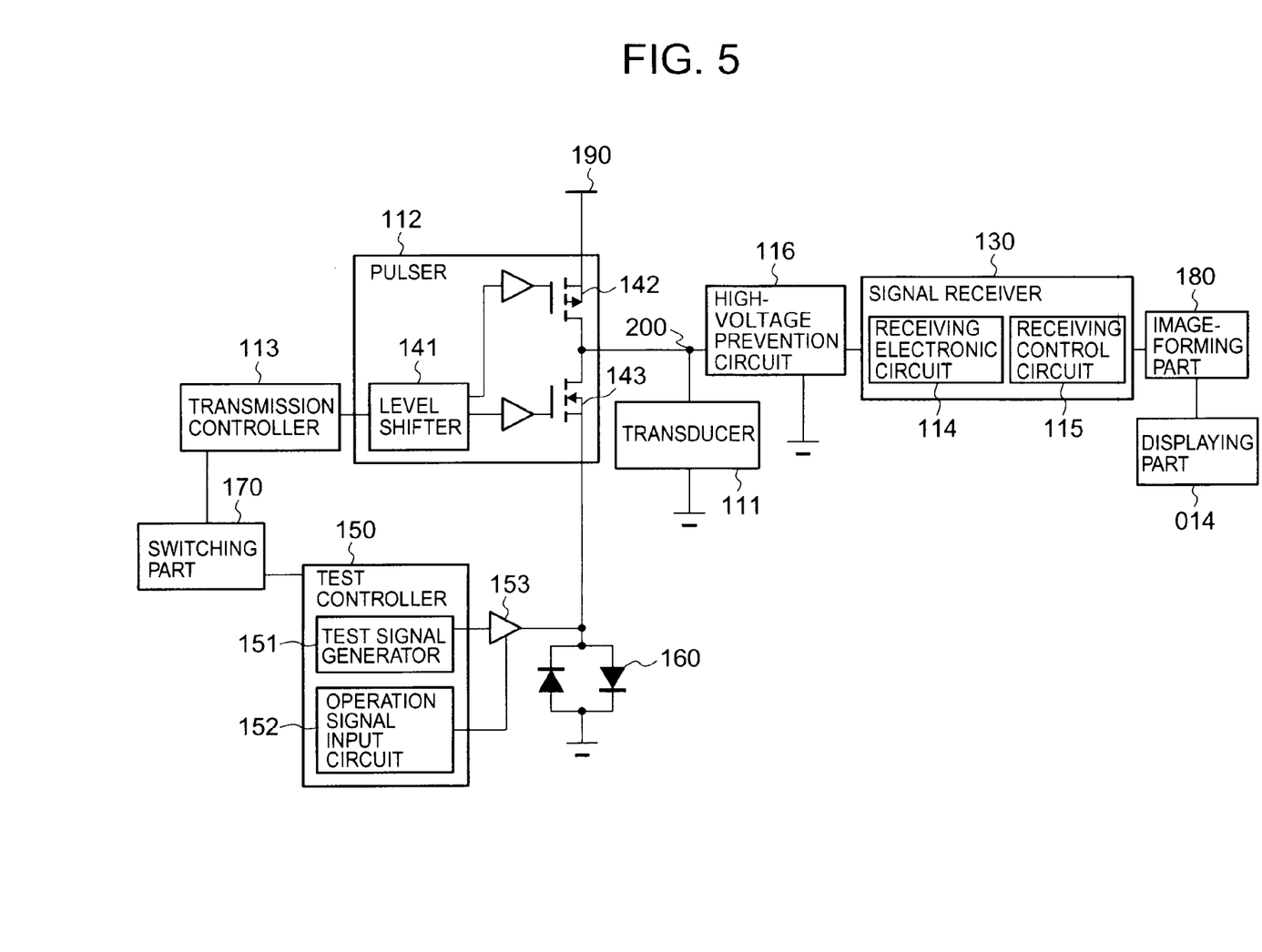
FIG. 5 is a block diagram of the ultrasonic imaging apparatus according to the first embodiment.

FIG. 4 is a configuration diagram that represents an example of the ultrasonic imaging apparatus according to the present invention. FIG. 5 is a block diagram that represents the functions of the ultrasonic imaging apparatus according to the present embodiment. In addition, FIG. 5 is a diagram that shows the configuration of a circuit that transmits/receives an ultrasonic wave for one channel corresponding to one transducer 111.

The ultrasonic imaging apparatus according to the present embodiment has two operational modes: an image-forming mode and a test mode. Operations in the image-forming mode are similar to those of the conventional ultrasonic imaging apparatus that has been explained in the background art. In other words, in FIG. 5, a block indicated by the same symbol as in FIG. 2 has the same functions. Now, hereinafter, an ultrasonic imaging apparatus according to the first embodiment in the test mode will be explained.

While only one transducer 111 is displayed in FIG. 5, the ultrasound probe 100 of the present embodiment actually has the same number of transducers 111 as contained in a 2-dimension array probe, that is, several thousands (represented as n×m in FIG. 1). The pulser 112 is a signal transmitter. The pulser 112 and the transducer 111 are connected to each other at the connection point 200. In addition, the signal receiver 130 is also connected to the connection point 200 through the high-pressure prevention circuit 116.

The switching part 170 is connected to the transmission controller 113 and the test controller 150. Then, upon receiving from the body control circuit 015 a switching command for the test mode that an operator has entered from the inputting part 020, the switching part 170 switches the transmission controller 113 and the test controller 150 to the test mode. Incidentally, the ultrasonic diagnostic apparatus according to the present embodiment is normally set in the image-forming mode, and operations to be performed in this case are similar to the operations in FIG. 2 that have been explained in the related art.

The pulser 112 has a level shifter 141, a pulse production FET 142, and a shunt FET 143. The pulse production FET 142 is the first switching element. The shunt FET 143 is the second switching element. Herein, only one pulser 112 is described in FIG. 4, but actually the same number of pulsers 112 as are in the transducers 111 are disposed for each channel thereof.

Upon receiving the command to switch to test mode from the switching part 170, the transmission controller 113 enters into the pulser 112 a signal for controlling the test mode. Due to this signal, a high-voltage power supply 190 for transmission VTX is blocked and the pulse production FET 142 is switched off. Furthermore, due to this signal, the shunt FET 143 is switched on and an output point of the test signal outputting part 153 is connected to an output point of the pulser 112, that is, the connection point 200. Meanwhile, when the pulse production FET 142 is off, the impedance on the side of the level shifter 141 viewed from the connection point 200 is high.

The test controller 150 has a test signal generator 151 and an operation signal input circuit 152. Herein, only one test controller 150 is disposed in the present embodiment in order to reduce the occupation rate of the volume of the ultrasound probe 100, but a plurality of test controllers 150 may also be disposed.

Upon receiving the command to switch to test mode from the switching part 170, the test controller 150 instructs the test signal generator 151 to produce a test signal. Herein, the test signal is preferably a signal equivalent to the signal level of an ultrasonic echo. The signal level of the ultrasonic echo is a low-amplitude signal. Therefore, the test signal generator 151 produces, for example, a 2.5 MHz and 10 mVpp sine wave as a test signal.

In addition, upon receiving the command to switch to test mode from the switching part 170, the test controller 150 instructs the operation signal input circuit 152 to enter an operation signal into the test signal outputting part 153.

Upon receiving the operation signal from the operation signal input circuit 152, the test signal outputting part 153 switches into operating state. Then, the test signal outputting part 153 outputs the received test signal at low impedance. Only one test signal outputting part 153 is displayed in FIG. 4, but actually the number of such parts disposed for each channel is equivalent to the number of transducers 111.

The limiter 160 has two diodes located opposite to each other. These diodes become conductive when the input voltage is equal to or greater than the forward voltage drop of diodes, 1 V. Therefore, signals having a voltage of 1 V or more are grounded so as not to be sent to the shunt FET 143. As a result, test signals equal to or less than 1 V head for the shunt FET 143. In addition, a high-voltage pulse outputted from the pulser 112 in the image-forming mode has a voltage greater than 1 V. Thus, that high-voltage pulse is grounded through the limiter 160. As a result, the shunt FET 143 in the image-forming mode operates normally and the test signal outputting part 153 that is not used in the image-forming mode is protected from that high-voltage pulse. Herein, in the present embodiment, a limit value of the limiter 160 is configured to be 1 V because a signal of 1 V or less is used as a test signal equivalent to the signal level of the ultrasonic echo. In this regard, however, it is preferable to be set depending on the signal to be used and the degree of protection of the test signal outputting part 153. Herein, only one limiter 160 is displayed in FIG. 4, but actually the number of such parts disposed for each channel is equivalent to the number of transducers 111.

The high-pressure prevention circuit 116 is composed of a diode. The high-pressure prevention circuit 116 does not conduct the high-voltage pulse outputted from the pulser 112 when transmitting an ultrasound beam in the image-forming mode. On the other hand, the high-pressure prevention circuit 116 conducts a low-amplitude ultrasonic echo and a test signal when receiving an ultrasound beam in the image-forming mode. Herein, FIG. 4 shows displaying only one high-pressure prevention circuit 116, but such parts as many as the part for transducers 111 are actually disposed for each channel.

The signal receiver 130 has a receiving electronic circuit 114 and a receiving control circuit 115. A group of receiving electronic circuits 114 receives a test signal outputted from the test controller 150 and coming through the connection point 200, amplifies the entered test signal, and adjusts gain or the like. Then, the group of receiving electronic circuits 114 transmits the test signal to an image-forming part 180. The receiving control circuit 115 controls each operation, such as the amplification and gain adjustment, in the receiving electronic circuit 114. Herein, FIG. 4 shows displaying only one receiving electronic circuit 114, but such parts as many as the part for transducers 111 are actually disposed for each channel.

The image-forming part 180 is housed in the ultrasonic imaging apparatus body 010 shown in FIG. 4. Furthermore, the image-forming part 180 has a group of receiving electronic circuits of the body 011, a signal-processing circuit of the body 012, an image-processing circuit 013, and so forth. In addition, the image-processing circuit 013 has a DSP (Digital Signal Prossesor).

In the DSP included in the image-forming part 180 according to the present embodiment, regarding signal amplitude, wave frequency, and wave distortion, threshold values are stored in advance. For example, a threshold such as 30 mV±10% for amplitude is stored therein. In addition, for the threshold of the frequency or distortion, a threshold such as 10 dB, compared to the test signal from which a secondary or tertiary harmonic component has been outputted at the test signal outputting part 153, is stored. This allows the image-forming part 180 to determine it to be abnormal when it is a waveform of above or below a predetermined amplitude or when there are many higher harmonic waves other than a predetermined frequency component.

Upon receiving a test signal, the image-forming part 180 uses the DSP included in the image-processing circuit 013 for a frequency analysis. Then, the image-forming part 180 determines whether the amplitude or the distortion of frequency in the analysis results exceeds the stored threshold. When it exceeds the threshold, the image-forming part 180 instructs the displaying part 014 to display a notification of an abnormal detection and a waveform of the test signal received from the channel in which the abnormality has occurred. Herein, in the present embodiment, a waveform only from the channel in which the abnormality occurs is displayed so that it is easy to see the notification of the abnormal detection. In this regard, however, this may be displayed using another method, and it is also possible to display all waveforms or to display waveforms from a plurality of channels, for example.

As described above, a test signal is outputted in the test signal outputting part 153, passes through the shunt FET 143 because the shunt FET 143 is switched on, passes through the high-voltage-prevention circuit 116, runs through the signal receiver 130, and is analyzed in the image-forming part 180.

The image-forming part 180 comprises a test program in the DSP for performing image processing and conducts a test by executing this test program. This test includes two kinds of tests. One is a test for calibrating the image-forming part 180 itself and the other is a test of portions other than each functional part included in the ultrasonic imaging apparatus body 010 through which a test signal according to the present invention is passed.

Herein, the image-forming part 180 is housed in the ultrasonic imaging apparatus body 010, so the test for calibrating the image-forming part 180 itself can be conducted by using the test program of the ultrasonic imaging apparatus body 010. Therefore, the ultrasonic imaging apparatus body 010 including the image-forming part 180 can be maintained in a normal state independently from the ultrasound probe 100.

Thus, firstly the image-forming part 180 is set to its normal state and then the ultrasound probe 100 is operated according to the present invention in test mode. Accordingly, it is possible to conduct tests of portions other than each functional part included in the ultrasonic imaging apparatus body 010 through which a test signal has passed. In other words, by using the test described above, it is possible to check, for each channel thereof, the switching and driving of the pulse production FET 142, the switching and driving of the shunt FET 143, control of the pulse production FET 142 and the shunt FET 143 through the transmission controller 113, and the operations of the signal receiver 130.

Figure 6:
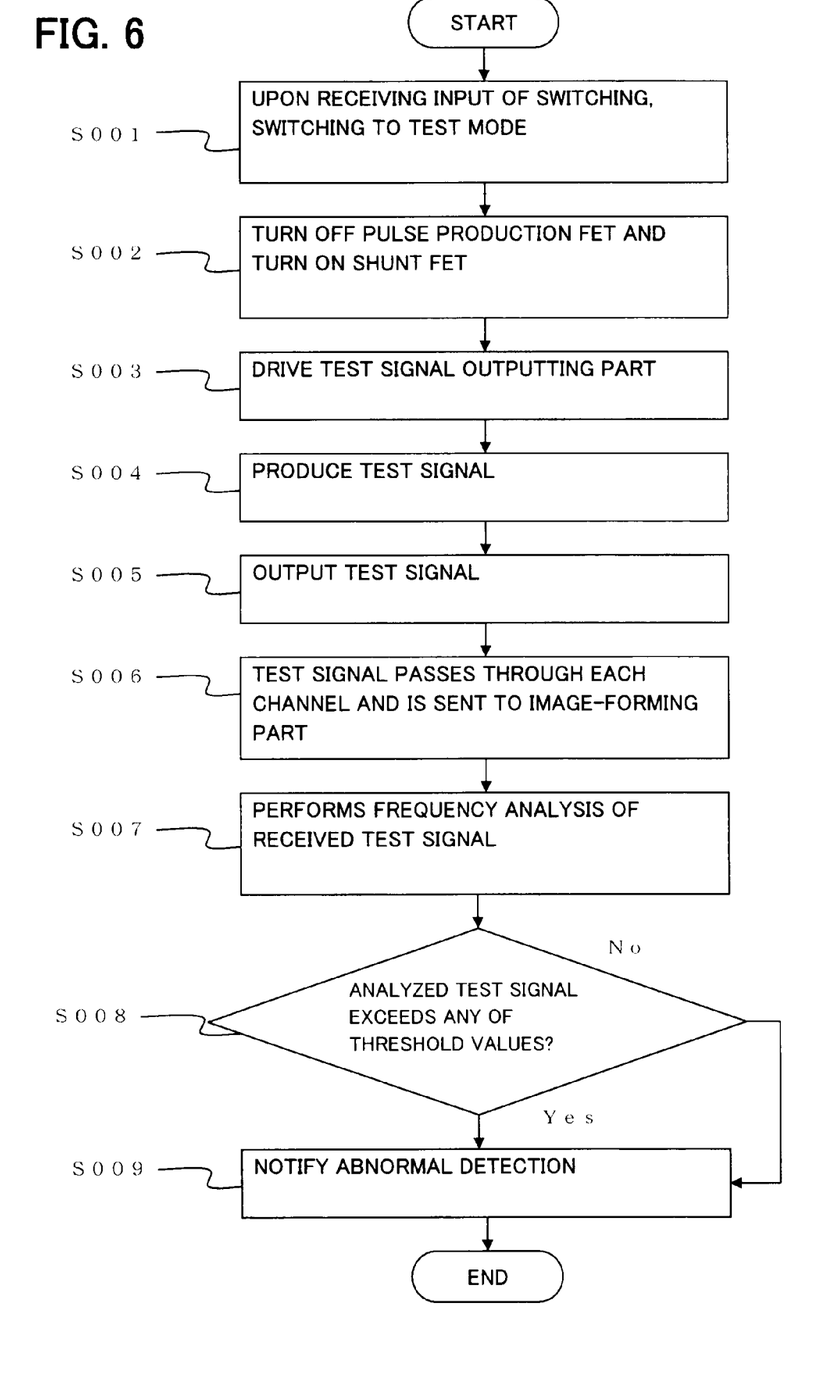
FIG. 6 is a diagram of a flow chart of the test mode in the ultrasonic imaging apparatus according to the first embodiment.

Next, operations of the ultrasonic imaging apparatus according to the present embodiment in test mode will be explained with reference to FIG. 6. FIG. 6 is a diagram of a flow chart of the test mode in the ultrasonic imaging apparatus according to the present embodiment.

Step S001: An operator enters switching to test mode by means of the inputting part 020. Upon receiving the input of switching, the body control circuit 015 instructs the switching part 170 to switch to test mode. The switching part 170 instructs the transmission controller 113 and the test controller 150 to switch to test mode.

Step S002: The transmission controller 113 turns off the pulse production FET 142 and turns on the shunt FET 143.

Step S003: The test controller 150 instructs the operation signal input circuit 152 to transmit an operation signal to the test signal outputting part 153. The test signal outputting part 153 switches into the operating state.

Step S004: The test controller 150 instructs the test signal generator 151 to produce a test signal at a level equivalent to an ultrasonic echo and transmits the test signal to the test signal outputting part 153.

Step S005: The test signal outputting part 153 outputs the test signal at low impedance.

Step S006: The test signal passes through the shunt FET 143, the high-voltage-prevention circuit 116, and the signal receiver 130 in each channel and is sent to the image-forming part 180.

Step S007: The image-forming part 180 performs a frequency analysis of the received test signal using the DSP.

Step S008: The DSP determines whether the analyzed test signal exceeds any of the threshold values. Go to Step S009 when there is a channel that exceeds its threshold, or end the test if none of the channels exceed their threshold.

Step S009: The image-forming part 180 instructs the displaying part 014 to display a notification of an abnormal detection and information on the channel in which the abnormality has been detected.

As described above, in the ultrasonic imaging apparatus according to the present embodiment, a test signal is produced from the ultrasound probe, so it is possible to conduct a test of the pathway in the signal transmitter, the signal receiver, and each channel without using a water tank, target, etc. for the test. Therefore, it is possible to readily conduct the test and thus contribute to reductions of erroneous diagnoses and medical malpractice due to failures of ultrasound probes comprising a transmitter/receiver.

Second Embodiment

Figure 7:
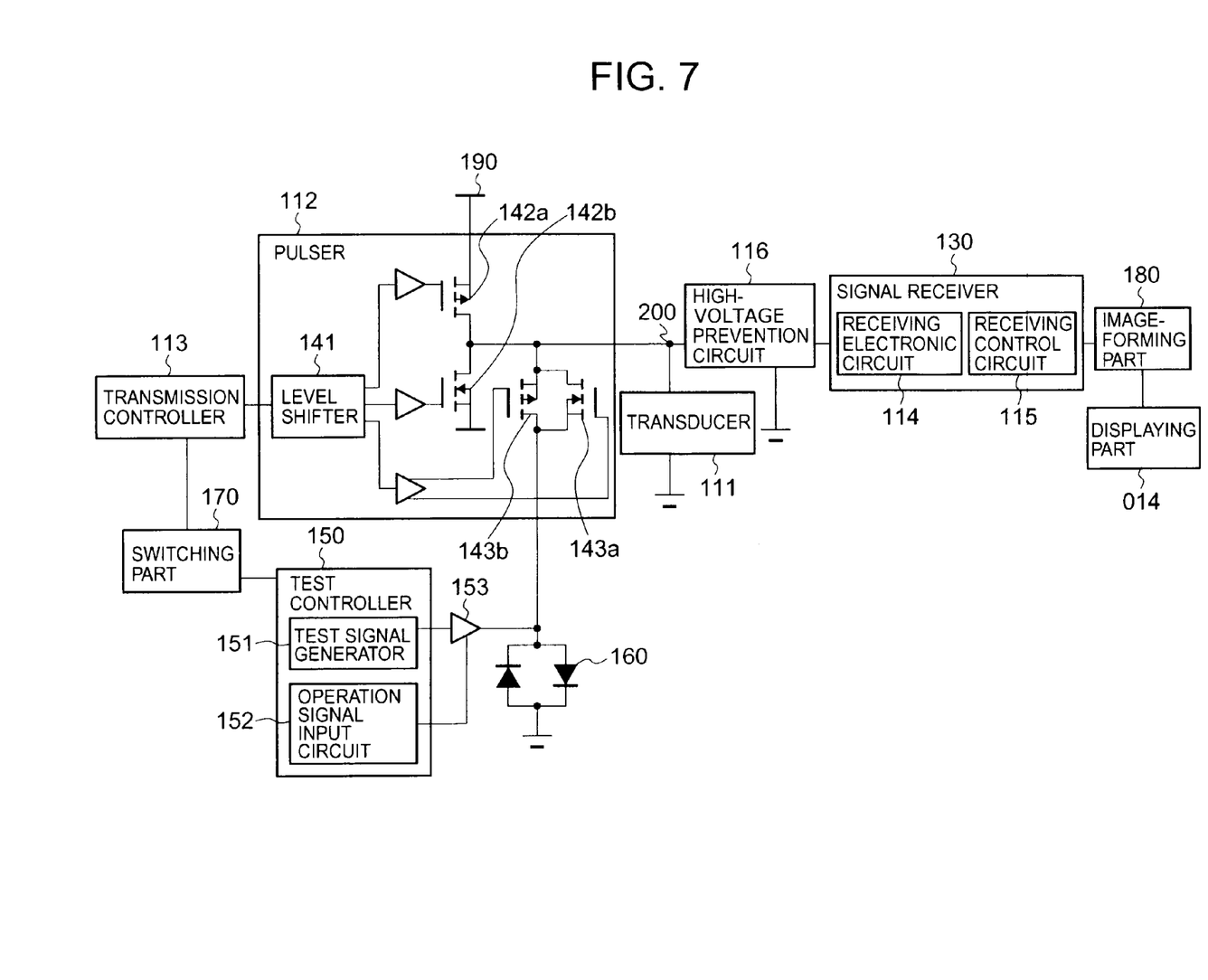
FIG. 7 is a block diagram of the ultrasonic imaging apparatus according to the second embodiment.

For the second embodiment, a configuration for the ultrasonic imaging apparatus of the first embodiment is also applied, and further a bipolar pulser is used. The present embodiment is similar to the first embodiment for operations of portions other than the bipolar pulser, so the bipolar pulser in test mode will be explained below. FIG. 7 is a block diagram that represents the functions of the ultrasonic imaging apparatus according to the second embodiment.

The transmission controller 113 sends, to the pulser 112, a signal for turning off the pulse production FET 142 and turning off the shunt FET 143 upon receiving a command to switch to test mode from the switching part 170.

The pulser 112 has a level shifter 141, a positive pole pulse generator 142a for producing a positive pole pulse, a negative pole pulse generator 142b for producing a negative pole pulse, a shunt FET 143a corresponding to the positive pole pulse production FET 142a, and a shunt FET 143b corresponding to the negative pole pulse production FET 142b.

Upon receiving a command from the transmission controller 113, the pulser 112 turns off the positive pole pulse production FET 142a and the negative pole pulse production FET 142b; that is, it puts them into high impedance. Furthermore, the pulser 112 turns on both shunt FET 143a and shunt FET 143b. Herein, in the present embodiment, both the shunt FET 143a and the shunt FET 143b are turned on; that is, a test signal from the test controller 150 is sent to the connection point 200. However, this means that it switches to test mode when the output point of the test signal outputting part 153 is connected to the output point of the pulser 112, so it may also be configured to turn on either one of shunt FET 143a or the shunt FET 143b.

When the pulser 112 is operating as described, a test signal outputted from the test signal outputting part 153 passes through the shunt FET 143a or the shunt FET 143b, the high-pressure prevention circuit 116, and the signal receiver 130, and is then sent to the image-forming part 180.

As described above, the operations of the ultrasonic imaging apparatus according to the present embodiment as described make it possible to, even when using a bipolar pulser, conduct a test of each channel by using a test signal outputted from the test signal outputting part without using a water tank, target, etc. for conducting the test. This makes it possible to readily test also the ultrasonic imaging apparatus using the bipolar pulser.

What is claimed is:

1. An ultrasound probe, comprising:
a plurality of signal transmitters respectively configured to produce a pulse current by repeatedly switching the connection state of a switching element;
a plurality of ultrasonic transducers respectively configured to transmit an ultrasonic pulse to a subject to be examined upon receiving said pulse current, and to produce a receiving current upon receiving the reflected wave;
a signal receiver configured to receive said receiving current; and
a test signal generator configured to produce a test signal and to output said test signal to a connection point of said signal transmitter, said ultrasonic transducer, and said signal receiver by switching said connection state of said switching element to a state through which said test signal is conducted.

2. An ultrasound probe, comprising:
a transducer, disposed at a predetermined connection point, configured to receive a pulse signal and to send out an ultrasound beam to a subject to be examined;
a signal transmitter configured to produce an ultrasonic pulse from said connection point; and
a signal receiver configured to receive a signal that is based on an ultrasonic echo from said connection point, wherein the ultrasound probe comprises:
a switching part configured to switch two operation modes consisting of an image-forming mode and a test mode;
a transmission controller configured to supply said pulse signal from said signal transmitter to said connection point when instructing said transducer to produce said ultrasonic pulse in said image-forming mode, wherein the transmission controller is configured to turn off said signal transmitter in a high output impedance state when instructing said transducer to receive the ultrasonic echo reflected by the subject to be examined in said image-forming mode, and is configured to turn off said signal transmitter in a high output impedance state in said test mode;
a test signal outputting part configured to output a test signal to said connection point; and
a test controller configured to turn off the output of said test signal from said test signal outputting part in said image mode, wherein the test controller is configured to instruct said test signal outputting part to output said test signal in said test mode.

3. An ultrasound probe, comprising:
a transducer, disposed at a predetermined connection point, configured to receive a pulse signal and to send out an ultrasonic beam to a subject to be examined;
a signal transmitter having a first switching element and a second switching element that are connected to said connection point in parallel, the signal transmitter being configured to pulse-drive both said first switching element and said second switching element when instructing said transducer to produce an ultrasonic pulse and configured to turn off said first switching element and said second switching element when instructing said transducer to receive the ultrasonic echo reflected by the subject to be examined; and
a signal receiver configured to receive a signal that is based on said ultrasonic echo from said connection point, wherein the ultrasound probe further comprises:
a switching part configured to switch between two operation modes consisting of an image-forming mode and a test mode;

a test signal outputting part that is connected between said second switching element and ground in series, wherein the test signal outputting part is configured to output a test signal;

a limiter that is connected to said test signal outputting part in parallel, configured to pass a signal outputted from said test signal outputting part through said second switching element;

a transmission controller configured to turn off said first switching element and to turn on said second switching element in said test mode; and a test controller configured to operate said test signal outputting part to send out said test signal to said signal receiver in said test mode.

4. An ultrasonic imaging apparatus, comprising an ultrasound probe comprising:

a transducer, disposed at a predetermined connection point, configured to receive a pulse signal and to send out an ultrasound beam to a subject to be examined;

a signal transmitter having a first switching element and a second switching element that are connected to said connection point in parallel, the second switching element being configured to pulse-drive both said first switching element and said second switching element when instructing said transducer to produce an ultrasonic pulse and configured to turn off said first switching element and said second switching element when instructing said transducer to receive the ultrasonic echo reflected by said subject to be examined; and a signal receiver configured to receive a signal that is based on said ultrasonic echo from said connection point, and an image-generating part configured to generate an ultrasonic image based on the signal received from said ultrasound probe and to display the same on a displaying part, wherein said ultrasound probe further comprises:

a switching part configured to switch between two operation modes consisting of an image-forming mode and a test mode;

a test signal outputting part, connected between said second switching element and ground in series, configured to output a test signal, a limiter, connected to said test signal outputting part in parallel, configured to obtain a signal outputted from a test signal generator through said second switching element;

a transmission controller configured to turn off said first switching element and to turn on said second switching element in said test mode; and a test controller configured to operate said test signal outputting part to send out said test signal to said signal receiver in said test mode, and wherein said image-forming part is configured to compare said test signal received from said signal receiver with a threshold stored in advance and to instruct said displaying part to display a warning in test mode when exceeding said threshold.

5. The ultrasonic imaging apparatus according to claim 4, wherein said test controller is configured to output a signal equivalent to the signal level of said ultrasonic echo.

6. The ultrasonic imaging apparatus according to claim 4, wherein said ultrasound probe is a 2-dimension array on which ultrasonic transducers are arranged 2-dimensionally.

7. The ultrasonic imaging apparatus according to claim 5, wherein said ultrasound probe is a 2-dimension array on which ultrasonic transducers are arranged 2-dimensionally.

8. The ultrasonic imaging apparatus according to claim 4, wherein when instructing said transducer to produce an ultrasonic pulse in said image-forming mode, said first switching element is configured to repeatedly switch on/off at a constant interval to turn on said second switching element when said first switching element is off.

9. The ultrasonic imaging apparatus according to claim 5, wherein when instructing said transducer to produce an ultrasonic pulse in said image-forming mode, said first switching element is configured to repeatedly switch on/off at a constant interval to turn on said second switching element when said first switching element is off.

10. The ultrasonic imaging apparatus according to claim 6, wherein when instructing said transducer to produce an ultrasonic pulse in said image-forming mode, said first switching element is configured to repeatedly switch on/off at a constant interval to turn on said second switching element when said first switching element is off.

11. An ultrasound probe, comprising:

a transducer, disposed at a predetermined connection point, configured to receive a pulse signal having a polarity of positive and negative and to send out an ultrasound beam to a subject to be examined;

a signal transmitter having two first switching elements and two second switching elements, the two first switching elements being connected to said connection point in parallel and respectively having polarity of positive and negative, two second switching elements pairing with said first switching elements, wherein the signal transmitter is configured to pulse-drive both said two first switching elements and said two second switching elements when instructing said transducer to produce an ultrasonic pulse, wherein the signal transmitter is configured to turn off said two first switching elements and said two second switching elements when instructing said transducer to receive the ultrasonic echo reflected by the subject to be examined; and a signal receiver configured to receive a signal that is based on said ultrasonic echo from said connection point, wherein said ultrasound probe further comprises:

a switching part configured to switch between two operation modes consisting of an image-forming mode and a test mode;

a test signal outputting part that is connected between said second switching element and ground in series, configured to output a test signal;

a limiter that is connected to said test signal outputting part in parallel, configured to obtain a signal sent from a test signal generator through said second switching element;

a transmission controller configured to turn off both said two first switching elements and to turn on any one or both of said two second switching elements in said test mode; and a test controller configured to operate said test signal outputting part to send out said test signal to said signal receiver in said test mode.

* * * * *